(12) United States Patent
Gawryl et al.

(10) Patent No.: US 7,041,800 B1
(45) Date of Patent: *May 9, 2006

(54) PRESERVING A HEMOGLOBIN BLOOD SUBSTITUTE WITH A TRANSPARENT OVERWRAP

(75) Inventors: Maria S. Gawryl, East Boston, MA (US); Robert A. Houtchens, Milford, MA (US); William R. Light, Natick, MA (US)

(73) Assignee: Biopure Corporation, Cambridge, MA (US)

( * ) Notice: Subject to any disclaimer, the term of this patent is extended or adjusted under 35 U.S.C. 154(b) by 282 days.

This patent is subject to a terminal disclaimer.

(21) Appl. No.: 10/018,599

(22) PCT Filed: Jul. 7, 2000

(86) PCT No.: PCT/US00/18747

§ 371 (c)(1),
(2), (4) Date: May 22, 2002

(87) PCT Pub. No.: WO01/01775

PCT Pub. Date: Jan. 11, 2001

Related U.S. Application Data

(63) Continuation of application No. 09/348,881, filed on Jul. 7, 1999, now Pat. No. 6,288,027, which is a continuation-in-part of application No. 09/173,189, filed on Oct. 14, 1998, now Pat. No. 6,271,351, which is a continuation-in-part of application No. 08/974,658, filed on Nov. 19, 1997, now abandoned, which is a continuation of application No. 08/471,583, filed on Jun. 7, 1995, now Pat. No. 5,691,452, which is a continuation-in-part of application No. 08/458,916, filed on Jun. 2, 1995, now Pat. No. 5,840,852, which is a continuation of application No. 08/409,337, filed on Mar. 23, 1995, now Pat. No. 5,854,209.

(51) Int. Cl.
C07K 14/805 (2006.01)
A61B 19/02 (2006.01)

(52) U.S. Cl. .................... 530/385; 514/6; 604/403; 604/408

(58) Field of Classification Search ............... 530/385; 514/6; 604/403, 408
See application file for complete search history.

(56) References Cited

U.S. PATENT DOCUMENTS

| | | | |
|---|---|---|---|
| 4,001,200 A | 1/1977 | Bonsen et al. |
| 4,001,401 A | 1/1977 | Bonsen et al. |
| 4,053,590 A | 10/1977 | Bonsen et al. |
| 4,061,736 A | 12/1977 | Morris et al. |
| 4,140,162 A | 2/1979 | Gajewski et al. |
| 4,460,365 A | 7/1984 | Ganshirt et al. |
| 4,561,110 A | 12/1985 | Herbert |
| 4,670,417 A | 6/1987 | Iwasaki et al. |
| 4,699,816 A | 10/1987 | Galli |
| 4,778,697 A | 10/1988 | Genske et al. |
| 4,826,811 A | 5/1989 | Sehgal |
| 4,826,955 A | 5/1989 | Akkapeddi et al. |
| 4,857,636 A | 8/1989 | Hsia |
| 4,861,867 A | 8/1989 | Estep |
| 5,045,529 A | 9/1991 | Chiang |
| 5,051,353 A | 9/1991 | Stratton et al. |
| 5,084,558 A | 1/1992 | Rausch et al. |
| 5,100,401 A | 3/1992 | Patel |
| 5,167,657 A | 12/1992 | Patel |
| 5,178,884 A | 1/1993 | Goodrich et al. |

(Continued)

FOREIGN PATENT DOCUMENTS

DE    39 15252 A    11/1990

(Continued)

OTHER PUBLICATIONS

Antonini, E. et al., "Sickling and Hemoglobin S Gelation," In *Methods in Enzymology vol. 76 Hemoglobins*, eds. (NY:Academic Press), pp. 765, 769-770 (1981).

(Continued)

*Primary Examiner*—Anish Gupta
(74) *Attorney, Agent, or Firm*—Hamilton, Brook, Smith & Reynolds, P.C.

(57) ABSTRACT

The invention relates to a method for preserving the stability of a hemoglobin blood substitute comprising maintaining the hemoglobin blood substitute in an atmosphere substantially free of oxygen. The method for preserving a deoxygenated hemoglobin blood substitute comprises maintaining the deoxygenated hemoglobin blood substitute in an oxygen barrier film overwrap package. In one embodiment, the package comprises a transparent laminate material comprising an oxygen barrier layer and a polyolefin layer, wherein the laminant has a thickness of between about 0.001 and about 0.01 inches (or about 0.0254 to about 0.254 millimeters) and an oxygen permeability of less than about 0.01 cubic centimeters per 100 square inches (or about 0.01 cc per 645 square centimeters) over 24 hours at 1 atmosphere and at about 23° C. The oxygen barrier layer comprises ethylene vinyl alcohol. Aso provided herein is a preserved deoxygenated hemoglobin blood substitute comprises a deoxygenated hemoglobin blood substitute and an oxygen barrier film overwrap package. The package comprises a transparent laminant material comprising an oxygen barrier layer and a polyolefin layer. Said oxygen barrier layer has an oxygen permeability of less than about 0.01 cubic centimeters per 100 square inches (or about 0.01 cc per 645 square centimeters) over 24 hours at 1 atmosphere and at about 27° C. room temperature, wherein the deoxygenated hemoglobin blood substitute is sealed within the overwrap package. In one embodiment, the oxygen barrier layer comprises ethylene vinyl alcohol.

9 Claims, No Drawings

U.S. PATENT DOCUMENTS

| | | |
|---|---|---|
| 5,189,146 A | 2/1993 | Hsia |
| 5,194,590 A | 3/1993 | Sehgal et al. |
| 5,234,903 A | 8/1993 | Nho et al. |
| 5,264,555 A | 11/1993 | Shorr et al. |
| 5,281,360 A | 1/1994 | Hong et al. |
| 5,296,465 A | 3/1994 | Rausch et al. |
| 5,296,466 A | 3/1994 | Kilbourn et al. |
| 5,322,161 A | 6/1994 | Shichman et al. |
| 5,334,706 A | 8/1994 | Przybelski |
| 5,352,773 A | 10/1994 | Kandler et al. |
| 5,356,709 A | 10/1994 | Woo et al. |
| 5,439,882 A | 8/1995 | Feola et al. |
| 5,683,768 A | 11/1997 | Shang et al. |
| 5,929,031 A | 7/1999 | Kerwin et al. |
| 6,127,043 A | 10/2000 | Lange |

FOREIGN PATENT DOCUMENTS

| | | |
|---|---|---|
| GB | 2 107 191 A | 4/1983 |
| JP | 06249848 | 9/1994 |
| WO | WO 89/12456 | 12/1989 |

OTHER PUBLICATIONS

Biro, G.P. et al., "Early Deleterious Hemorheologic Changes Following Acute Experimental Coronary Occlusion and Salutary Antihyperviscosity Effect of Hemodilution with Stroma-Free Hemoglobin," *American Heart Journal*, 103(5) :870-878 (1992).

Biro, G.P. and Beresford-Kroeger, D., "The Effect of Hemodilution with Stroma-Free Hemoglobin and Dextran on Collateral Perfusion of Ischemic Myocardium in the Dog," *American Heart Journal*, 99(1) :64-75 (1980).

Chu, D., et al., Abstract 80.13., "The Effect of Hemodilution with a Purified Monomer or Purified Bovine Hemoglobin on Infarct Size in Focal Ischemia in Rabbits," *Society for Neuroscience Abstracts*, 20:180 (1994), presented at the 24th Annual Meeting Society of Neuroscience, Miami Beach, FL (Nov. 13-18, 1994).

Cole, D. J. et al., "Focal Cerebral Ischemia in Rats: Effect of Hypervolemic Hemodilution with Disapirin Cross-Linked Hemoglobin versus Albumin on Brain Injury and Edema," *Anesthesiology*, 78(2):335-342 (1993).

Cole, D. J. et al., "Focal Cerebral Ischemia in Rats: Effect of Hemodilution with α-α Cross-Linked Hemoglobin on CBF," *J. Cereb. Blood Flow Metab.*, 12 (6) :971-976 (1992).

Cole, D. J. et al., "Effects of Viscosity and Oxygen Content on Cerebral Blood Flow in Ischemic and Normal Rat Brain," *Journal of Neurological Sciences*, 124:15-20 (1994).

DeVenuto, F., "Stability of Hemoglobin Solution During Extended Storage," *J. Lab. Clin. Med.*, 92(6) :946-952 (Dec. 1975).

Dodrill, R. et al., "Barrier Coated Polyester Films for Healthcare Packaging," Conference Paper Presented at the Polyester in Healthcare Packaging, pp. 1-17 [online] (1996) [retrieved on Apr. 28, 1999] Retrieved from the Internet <URL:http://www.rollprint.com/news/barrier.htm>.

Feola, M. et al., "Clinical Trail of a Hemoglobin Based Blood Substitute in Patients with Sickle Cell Anemia," *SURGERY, Gynecology & Obstetrics*, 174:379-386 (1992).

Feola, M. et al., "Improved Oxygenation of Ischemic Mycardium by Hemodilution with Stroma-Free Hemoglobin Solution," *CHEST*, 75(3) :369-375 (1979).

"Film Preserves Blood Substitute," *Pharmaceutical & Medical Packaging News*, [online] (Jul. 1998) [retrieved on Oct. 28, 2002]. Retrieved from the Internet <URL:http://www.devicelink.com/pmpn/archive/98/07/012.html>.

Hamilton, P. et al., "Preparation of Hemoglobin Solutions for Intravenous Infusion," *Hemoglobin Solution*, pp. 455-463.

Hauser, C. J. and Shoemaker, W.C., "Hemoglobin Solution in the Treatment of Hemorrhagic Shock," *Critical Care Medicine*, 10(4) :283-287 (1982).

Homer, L.D. et al., "Oxygen Gradients Between Red Blood Cells in the Microcirculation," *Hypoxia Between Red Cells*, Academic Press, Inc. 308-323 (1981).

Krieter, H. et al., "Effects of stroma-free polymerized bovine hemoglobin solution on oxygen transport, Global and regional blood flow in a canine model of stepwise hemodilution," *Anesth. Anal.*, 78(2) S226 (1994).

Leone, B.J., and Spahn, D.R., "Anemia, Hemodilution, and Oxygen Delivery," *Anesth. Analg.* 75:651-653 (1992).

Paradis, N.A. et al., "Selective aortic perfusion and oxygenation: An effective adjunct to external chest compression-based cardiopulmonary resusitation," *J. American College of Cardiology*, 23(2), 497-504 (1994).

Sarelius, I.H., Cell and Oxygen Flow in Arterioles Controlling Capillary Perfusion *Am. J. Physiol.* 265 (Heart Circ. Physiol. 34): H1682-H1687 (1993).

Standl, T. et al., "Hemodynamics and Oxygen Transport During Complete Isovolemic Hemodilution With a New Ultrapurified Polymerized Bovine Hemoglobin Solution in a Dog Model," Paper presented at the Annual Meeting of the American Society of Anesthesiologists, Washington (1993) and at the Central European Congress of Anaesthesiology, Dresden (1993).

Teicher, B.A. et al., "Oxygenation of tumors by a hemoglobin solution," *J. Cancer Research and Clinical Onco* 120:85-90 (1993).

Tsai, A.G. and Intaglietta, M., "Local Tissue Oxygenation During Constant Red Blood Cell Flux: A Discrete Source Analysis of Velocity and Hematocrit Changes," *Microvascular Research*, 37:308-322 (1989).

Waschke, K. et al., "Local Cerebral Blood Flow and Glucose Utilization After Blood Exchange with A Hemoglobin-Based $O_2$ Carrier in Conscious Rats," *Amer. J. Physiol.*, 265, 1234-H1248 (Jun. 1993).

Wei, E.P. et al., "Effect of Local Change in $O_2$ Saturation of Hemoglobin on Cerebral Vasodilution from Hypoxia and Hypotension ," *Am. J. Physiol.*, 265 (Heart Circ. Physiol. 34) :H1439-H1443 (1993).

PRESERVING A HEMOGLOBIN BLOOD SUBSTITUTE WITH A TRANSPARENT OVERWRAP

RELATED APPLICATIONS

This application is a Continuation of U.S. patent application Ser. No. 09/348,881, filed on Jul. 7, 1999, now U.S. Pat. No. 6,288,027 which is a Continuation-in-Part of U.S. patent application Ser. No. 09/173,189, filed on Oct. 14, 1998, now U.S. Pat. No. 6,271,351 which is a Continuation-in-Part of U.S. patent application Ser. No. 08/974,658, filed on Nov. 19, 1997 now abandoned, which is a Continuation of U.S. patent application Ser. No. 08/471,583, filed Jun. 7, 1995 now issued U.S. Pat. No. 5,691,452, which is a Continuation-in-Part of U.S. patent application Ser. No. 08/458,916, filed Jun. 2, 1995 now issued U.S. Pat. No. 5,840,582, which is a Continuation of U.S. patent application Ser. No. 08/409,337, filed Mar. 23, 1995 now issued U.S. Pat. No. 5,854,209.

BACKGROUND OF THE INVENTION

There exists a need for a blood-substitute to treat or prevent hypoxia resulting from blood loss (e.g, from acute hemorrhage or during surgical operations), resulting from anemia (e.g., pernicious anemia or sickle cell anemia), or resulting from shock (e.g, volume deficiency shock, anaphylactic shock, septic shock or allergic shock).

The use of blood and blood fractions as in these capacities as a blood-substitute is fraught with disadvantages. For example, the use of whole blood often is accompanied by the risk of transmission of hepatitis-producing viruses and AIDS-producing viruses which can complicate patient recovery or result in patient fatalities. Additionally, the use of whole blood requires blood-typing and cross-matching to avoid immunohematological problems and interdonor incompatibility.

Human hemoglobin, as a blood-substitute, possesses osmotic activity and the ability to transport and transfer oxygen, but it has the disadvantage of rapid elimination from circulation by the renal route and through vascular walls, resulting in a very short, and therefore, a typically unsatisfactory half-life. Further, human hemoglobin is also frequently contaminated with toxic levels of endotoxins, bacteria and/or viruses.

Non-human hemoglobin suffers from the same deficiencies as human hemoglobin. In addition, hemoglobin from non-human sources is also typically contaminated with proteins, such as antibodies, which could cause an immune system response in the recipient.

Previously, at least four other types of blood-substitutes have been utilized, including perfluorochemicals, synthesized hemoglobin analogues, liposome encapsulated hemoglobin, and chemically-modified hemoglobin. However, many of these blood-substitutes have typically had short intravascular retention times, being removed by the circulatory system as foreign substances or lodging in the liver, spleen, and other tissues. Also, many of these blood-substitutes have been biologically incompatible with living systems.

Thus, in spite of the recent advances in the preparation of hemoglobin-based blood-substitutes, the need has continued to exist for a blood-substitute which has levels of contaminants, such as endotoxins, bacteria, viruses, phospholipids and non-hemoglobin proteins, which are sufficiently low to generally prevent an immune system response and any toxicological effects resulting from an infusion of the blood-substitute. In addition, the blood-substitute must also be capable of transporting and transferring adequate amounts of oxygen to tissues under ambient conditions and must have a good intravascular retention time.

Further, it is preferred that the blood-substitute 1) has an oncotic activity generally equivalent to that of whole blood, 2) can be transfused to most recipients without cross-matching or sensitivity testing, and 3) can be stored with minimum amounts of refrigeration for long periods.

The blood-substitute is typically packaged in a metal foil laminate overwrap having high $O_2$ and moisture barrier properties. The metal foil laminates are typically opaque, thus not allowing visual inspection of the product nor inspection of the integrity of the primary package. Furthermore, an opaque overwrap requires the use of a second label on the outside of the overwrap.

In the past, clear silicon containing laminates with high oxygen and moisture barrier properties have not been useful in automated packaging equipment because the stress on the material caused it to crack or otherwise lose barrier properties.

SUMMARY OF THE INVENTION

The present invention is drawn to a method for preserving a deoxygenated hemoglobin blood substitute comprising maintaining a packaged deoxygenated hemoglobin blood substitute in an oxygen barrier film overwrap package, wherein the overwrap package comprises a transparent laminate material comprising an oxygen barrier layer and a polyolefin layer, wherein the laminate has a thickness of between about 0.001 and about 0.01 inches (or about 0.0254 and about 0.254 millimeters) and an oxgen permeability of less than about 0.01 cubic centimeters per 100 square inches (or about 0.01 cc per 645 square centimeters) over 24 hours at 1 atmosphere and at room temperature (about 23° C.), wherein the oxygen barrier layer comprises ethylene vinyl alcohol. In one embodiment, the method comprises maintaining the deoxygenated hemoglobin blood substitute in an oxygen barrier film overwrap comprising a transparent laminate material having a thickness of between about 0.01 and about 0.005 inches (or about 0.254 and about 0.127 millimeters).

The present invention also is drawn to a preserved, deoxygenated hemoglobin blood substitute comprising a packaged deoxygenated hemoglobin blood substitute and a transparent oxygen barrier film overwrap package. In one embodiment, the transparent laminate material comprises an oxygen barrier layer and a polyolefin layer, said oxgen barrier layer having an oxygen permeability of less than about 0.01 cubic centimeters per 100 square inches (or about 0.01 cc per 645 square centimeters) over 24 hours at 1 atmosphere and at room temperature (about 23° C.) and wherein the oxygen barrier layer comprises ethylene vinyl alcohol. The packaged deoxygenated hemoglobin blood substitute is sealed within the overwrap package, thereby preserving the deoxygenated hemoglobin blood substitute in an environment that is substantially free of oxygen.

In one embodiment of the present invention, the transparent laminate material is used in combination with foil laminate material in automated packaging.

In one embodiment, an automated packaging machine manufactured by Tiromat (Avon, Mass.) has been used. The advantages of this invention are numerous. One advantage is that the hemoglobin stored according to the methods of this invention has a greater degree of purity and longer shelf-life.

High barrier overwraps provide an addition level of product quality even when high barrier primary packaging is employed. In addition, the transparent high barrier overwraps of the present invention provide extremely high oxygen and water vapor barrier properties but have no saran (polyvinylidene chloride, PVDC) layer. PVDC poses a medical waste problem because chlorinated products such as polycyclic aromatic hydrocarbons and hydrochloric acid are generated during incineration. Clear overwraps allow the label of the primary package to be seen. Therefore, a second label typically is not required on the overwrap. In addition, product quality inspection and primary package integrity can also be evaluated. Furthermore, as demonstrated for the first time herein, automation equipment can be used with the clear oxygen barrier laminates, allowing production of very large numbers of packages in a short period of time with very little human labor and without the loss of barrier properties. The blood-substitute remains stable at room temperature for periods of two years or more, a significant improvement over previous methods.

DETAILED DESCRIPTION OF THE INVENTION

The features and other details of the present invention will now be more particularly described and pointed out in the claims. It will be understood that the particular embodiments of the invention are shown by way of illustration and not as limitations of the invention. The principle features of this invention can be employed in various embodiments without departing from the scope of the present invention.

The invention relates to a method for preserving the stability of a hemoglobin blood substitute comprising maintaining the hemoglobin blood substitute in an atmosphere substantially free of oxygen. This method can be accomplished by maintaining the blood substitute in an oxygen-impermeable container, such as an oxygen barrier primary package, an oxygen barrier film overwrap (e.g., a bag), glass container (e.g., a vial) or a steel container. Where the primary package is an oxygen barrier film, the container can be manufactured from a variety of materials, including polymer films, (e.g., an essentially oxygen-impermeable polyester, ethylene vinyl alcohol (EVOH), or nylon), and laminates thereof. Where the container comprises an oxygen barrier overwrap, the overwrap can be manufactured from a variety of materials, including polymer films, (e.g., an essentially oxygen-impermeable polyester, ethylene vinyl alcohol (EVOH), or nylon) and laminates, such as a transparent laminate (e.g. a silicon oxide or EVOH containing laminate) or a metal foil laminate (e.g., a silver or aluminum foil laminate).

Where the overwrap is a film, such as a polyester film, the film can be rendered essentially oxygen-impermeable by a variety of suitable methods. In one embodiment, the film as manufactured is essentially oxygen-impermeable. Alternatively, where the polymeric material is not sufficiently oxygen-impermeable to meet the desired specifications, the film can be laminated or otherwise treated to reduce or eliminate the oxygen permeability.

In a preferred embodiment, a transparent laminate is employed for at least one face of the overwrap. In one embodiment, at least one layer of the transparent laminate is an oxygen barrier. The oxygen barrier layer preferably has a thickness between about 0.00011 and 0.001 inches (or about $2.54 \times 10^{-3}$ and 0.025 millimeters). For both the primary package and the overwrap, the laminate typically contains one or more polymeric layers. The polymer can be a variety of polymeric materials including, for example, a polyester layer (e.g., a 48 gauge polyester), nylon or a polyolefin layer, such as polyethylene, ethylene vinyl acetate, or polypropylene or copolymers thereof.

The overwraps of the invention can be of a variety of constructions, including vials, cylinders, boxes, etc. In a preferred embodiment, the container is in the form of a bag. A suitable bag can be formed by continuously bonding one or more (e.g., two) sheets at the perimeter(s) thereof to form a tightly closed, oxygen impermeable, construction having a fillable center. The shape of the bag can be those routinely encountered in that art. In the case of laminates comprising polyolefins, such as linear low density, low density, medium or high density polyethylene or polypropylene and copolymers thereof, the perimeter of the bag is bonded or sealed using heat. It is well within the skill of the art to determine the appropriate temperature to generate a tightly closed, oxygen and/or moisture impermeable construction.

The containers preferably have an oxygen permeability of less than about 0.01 cc per 100 square inches (or about 0.01 cc per 645 square centimeters) per 24 hours per atmosphere at room temperature, preferably less than about 0.005 cc per square inch (or about 0.005 cc per 6.45 square centimeters) at these conditions. Containers that meet these criteria include for example plastic containers with an overwrap, such as high barrier laminate containers with an overwrap constructed, for example, from polyolefin, such as polypropylene, ethylene vinyl alcohol and another layer of polyolefin such as linear low density polyethylene laminate. In one embodiment the laminate comprises polypropylene, EVOH and polypropylene copolymer at thicknesses of 1.8 mil, 1.2 mil and 3.0 mil respectively (or 0.046, 0.030 and 0.076 millimeters, respectively). The oxygen permeability of the high barrier laminate is 0.00153 cc per 100 square inch (or 0.0015 cc per 645 square centimeters per atmosphere per day at 25° C., 100%/50% relative humidity (RH)) (inside/outside) and water vapor transmission is about 0.354 mg per 100 square inches (or about 0.354 mg per 645 square centimeters) per atm per day (25° C., 100%/50% RH). These composite film overwrapped plastic bags are sealed using a Tiromat sealing apparatus (Avon, Mass.). In one embodiment, the overwrap comprises two sheets of transparent laminate material. In another embodiment, one sheet of the overwrap package comprises foil laminate material and another sheet comprises transparent laminate material. In another embodiment, the bottom sheet of the overwrap package is a foil laminate and is formed such that at least one dish shape or chamber is defined in the foil laminate. The hemoglobin blood substitute, in a primary package, is then placed into the chambers of the foil, with the label facing upward. The foil and hemoglobin blood substitute in primary packaging is then nitrogen purged and a vacuum pulled and the clear laminate is then heat sealed to the foil laminate bottom layer, creating an overwrapped hemoglobin blood substitute.

In a preferred embodiment, the blood substitute is packaged under an atmosphere which is substantially free of oxygen. Examples of suitable atmospheres include nitrogen, argon and helium.

As defined herein, a blood-substitute is a hemoglobin-based oxygen carrying composition for use in humans, mammals and other vertebrates, which is capable of transporting and transferring oxygen to vital organs and tissues, at least, and can maintain sufficient intravascular oncotic pressure. A vertebrate is as classically defined, including humans, or any other vertebrate animals which uses blood in a circulatory system to transfer oxygen to tissue. Additionally, the definition of circulatory system is as classically defined, consisting of the heart, arteries, veins and microcirculation including smaller vascular structures such as capillaries.

A blood-substitute of the invention preferably has levels of endotoxins, phospholipids, foreign proteins and other contaminants which will not result in a significant immune system response and which are non-toxic to the recipient.

Preferably, a blood-substitute is ultrapure. Ultrapure as defined herein, means containing less than 0.5 EU/ml of endotoxin, less than 3.3 nmoles/ml phospholipids and little to no detectable levels of non-hemoglobin proteins, such as serum albumin or antibodies.

The term "endotoxin" refers to the cell-bound lipopolysaccharides, produced as a part of the outer layer of gram-negative bacterial cell walls, which under many conditions are toxic. When injected into animals, endotoxins can cause fever, diarrhea, hemorrhagic shock, and other tissue damage. Endotoxin unit (EU) has been defined by the United States Pharmacopeial Convention of 1983, page 3014, as the activity contained in 0.1 nanograms of U.S. reference standard lot EC-5. One vial of EC-5 contains 10,000 EU. Examples of suitable means for determining endotoxin concentrations in a blood-substitute include the method "Kinetic/Turbidimetric Limuus Amebocytic Lysate (LAL) 5000 Methodology" developed by Associates of Cape Cod, Woods Hole, Mass.

Stable polymerized hemoglobin, as defined herein, is a hemoglobin-based oxygen carrying composition which does not substantially increase or decrease in molecular weight distribution and/or in methemoglobin content during storage periods at suitable storage temperatures for periods of two years or more, and preferably for periods of two years or more, when stored in a low oxygen environment. Suitable storage temperatures for storage of one year or more are between about 0° C. and about 40° C. The preferred storage temperature range is between about 0° C. and about 25° C.

A suitable low oxygen environment, or an environment that is substantially oxygen-free, is defined as the cumulative amount of oxygen in contact with the blood-substitute, over a storage period of at least about two months, preferably at least about one year, or more preferably at least about two years which will result in a methemoglobin concentration of less than about 15% by weight in the blood-substitute. The cumulative amount of oxygen includes oxygen inleakage into the blood-substitute packaging and the original oxygen content of the blood-substitute and packaging.

Throughout this method, from red blood cell (RBC) collection until hemoglobin polymerization, blood solution, RBCs and hemoglobin are maintained under conditions sufficient to minimize microbial growth, or bioburden, such as maintaining temperature at less than about 20° C. and above 0° C. Preferably, temperature is maintained at a temperature of about 15° C. or less. More preferably, the temperature is maintained at 10±2° C.

In this method, portions of the components for the process for preparing a stable polymerized hemoglobin blood-substitute are sufficiently sanitized to produce a sterile product. Sterile is as defined in the art, specifically, that the solution meets United States Pharmacopeia requirements for sterility provided in USP XXII, Section 71, pages 1483–1488. Further, portions of components that are exposed to the process stream, are usually fabricated or clad with a material that will not react with or contaminate the process stream. Such materials can include stainless steel and other steel alloys, such as Inconel.

Suitable RBC sources include human blood, bovine blood, ovine blood, porcine blood, blood from other vertebrates and transgenically-produced hemoglobin, such as the transgenic Hb described in *BIO/TECHNOLOGY,* 12: 55–59 (1994).

The blood can be collected from live or freshly slaughtered donors. One method for collecting bovine whole blood is described in U.S. Pat. Nos. 5,084,558 and 5,296,465, issued to Rausch et al. It is preferred that the blood be collected in a sanitary manner.

At or soon after collection, the blood is mixed with at least one anti coagulant to prevent significant clotting of the blood. Suitable anticoagulants for blood are as classically known in the art and include, for example, sodium citrate, ethylenediaminetetraacetic acid and heparin. When mixed with blood, the anticoagulant may be in a solid form, such as a powder, or in an aqueous solution.

It is understood that the blood solution source can be from a freshly collected sample or from an old sample, such as expired human blood from a blood bank.

Further, the blood solution could previously have been maintained in frozen and/or liquid state. It is preferred that the blood solution is not frozen prior to use in this method.

In another embodiment, prior to introducing the blood solution to anticoagulants, antibiotic levels in the blood solution, such as penicillin, are assayed. Antibiotic levels are determined to provide a degree of assurance that the blood sample is not burdened with an infecting organism by verifying, that the donor of the blood sample was not being treated with an antibiotic. Examples of suitable assays for antibiotics include a penicillin assay kit (Difco, Detroit, Mich.) employing a method entitled "Rapid Detection of Penicillin in Milk". It is preferred that blood solutions contain a penicillin level of less than or equal to about 0.008 units/ml. Alternatively, a herd management program to monitor the lack of disease in or antibiotic treatment of the cattle may be used.

Preferably, the blood solution is strained prior to or during the anticoagulation step, for example by straining, to remove large aggregates and particles. A 600 mesh screen is an example of a suitable strainer.

The RBCs in the blood solution are then washed by suitable means, such as by diafiltration or by a combination of discrete dilution and concentration steps with at least one solution, such as an isotonic solution, to separate RBCs from extracellular plasma proteins, such as serum albumins or antibodies (e.g., immunoglobulins (IgG)). It is understood that the RBCs can be washed in a batch or continuous feed mode.

Acceptable isotonic solutions are as known in the art and include solutions, such as a citrate/saline solution, having a pH and osmolarity which does not rupture the cell membranes of RBCs and which displaces the plasma portion of the whole blood. A preferred isotonic solution has a neutral pH and an osmolarity between about 285–315 mOsm. In a preferred embodiment, the isotonic solution is composed of an aqueous solution of sodium citrate dihydrate (6.0 g/l) and of sodium chloride (8.0 g/l).

Water which can be used in the method of invention includes distilled water, deionized water, water-for-injection (WFI) and/or low pyrogen water (LPW). WFI, which is preferred, is deionized, distilled water that meets U.S. Pharmacological Specifications for water-for-injection. WFI is further described in *Pharmaceutical Engineering,* 11, 15–23 (1991). LPW, which is preferred, is deionized water containing less than 0.002 EU/ml.

It is preferred that the isotonic solution be filtered prior to being added to the blood solution. Examples of suitable filters include a Millipore 10,000 Dalton ultrafiltration membrane, such as a Millipore Cat# CDUF 050 G1 filter or A/G Technology hollow fiber, 10,000 Dalton (Cat# UFP-10-C-85).

In a preferred embodiment, RBCs in the blood solution are washed by diafiltration. Suitable diafilters include microporous membranes with pore sizes which will separate RBCs from substantially smaller blood solution components, such as a 0.1 μm to 0.5 μm filter (e.g., a 0.2 μm hollow fiber filter, Microgon Krosflo II microfiltration cartridge). Concurrently, a filtered isotonic solution is added continuously (or in batches) as makeup at a rate equal to the rate (or volume) of filtrate lost across the diafilter. During RBC washing, components of the blood solution which are significantly smaller in diameter than RBCs, or are fluids such as plasma, pass through the walls of the diafilter in the filtrate. RBCs, platelets and larger bodies of the diluted blood solution, such as white blood cells, are retained and mixed with isotonic solution, which is added continuously or batchwise to form a dialyzed blood solution.

In a more preferred embodiment, the volume of blood solution in the diafiltration tank is initially diluted by the addition of a volume of a filtered isotonic solution to the diafiltration tank. Preferably, the volume of isotonic solution added is about equal to the initial volume of the blood solution.

In an alternate embodiment, the RBCs are washed through a series of sequential (or reverse sequential) dilution and concentration steps, wherein the blood solution is diluted by adding at least one isotonic solution, and is concentrated by flowing across a filter, thereby forming a dialyzed blood solution.

RBC washing is complete when the level of plasma proteins contaminating, the RBCs has been substantially reduced (typically at least about 90%). Typically, RBC washing is complete when the volume of filtrate drained from diafilter 34 equals about 300%, or more, of the volume of blood solution contained in the diafiltration tank prior to diluting the blood solution with filtered isotonic solution. Additional RBC washing may further separate extracellular plasma proteins from the RBCs. For instance, diafiltration with 6 volumes of isotonic solution may remove at least about 99% of IgG from the blood solution.

The dialyzed blood solution is then exposed to means for separating the RBCs in the dialyzed blood solution from the white blood cells and platelets, such as by centrifugation.

It is understood that other methods generally known in the art for separating RBCs from other blood components can be employed. For example, sedimentation, wherein the separation method does not rupture the cell membranes of a significant amount of the RBCs, such as less than about 30% of the RBCs, prior to RBC separation from the other blood components.

Following separation of the RBCs, the RBCs are lysed by a means for lysing RBCs to release hemoglobin from the RBCs to form a hemoglobin-containing solution. Lysis means can use various lysis methods, such as mechanical lysis, chemical lysis, hypotonic lysis or other known lysis methods which release hemoglobin without significantly damaging the ability of the Hb to transport and release oxygen.

In yet another embodiment, recombinantly produced hemoglobin, such as the recombinantly produced hemoglobin described in *Nature*, 356: 258–260 (1992), can be processed in the method of invention in place of RBCs. The bacteria cells containing the hemoglobin are washed and separated from contaminants as described above. These bacteria cells are then mechanically ruptured by means known in the art such as a ball mill, to release hemoglobin from the cells and to form a lysed cell phase. This lysed cell phase is then processed as is the lysed RBC phase.

Following lysis, the lysed RBC phase is then ultrafiltered to remove larger cell debris, such as proteins with a molecular weight above about 100,000 Daltons. Generally, cell debris include all whole and fragmented cellular components with the exception of Hb, smaller cell proteins, electrolytes, coenzymes and organic metabolic intermediates. Acceptable ultrafilters include, for example, 100,000 Dalton filters made by Millipore (Cat# CDUF 050 HI) and made by A/G Technology (Needham, Mass.; Model No. UFP100E55).

It is preferred that ultrafiltration continues until the concentration of Hb in the lysed RBC phase is less than 8 grams/liter (g/l) to maximize the yield of hemoglobin available for polymerization. Other methods for separating Hb from the lysed RBC phase can be employed, including sedimentation, centrifugation or microfiltration. The Hb ultrafiltrate can then be ultrafiltered to remove smaller cell debris, such as electrolytes, coenzymes, metabolic intermediates and proteins less than about 30,000 Daltons in molecular weight, and water from the Hb ultrafiltrate. Suitable ultrafilters include a 30,000 Dalton ultrafilter (Millipore Cat# CDUF 050 T1 and/or Armicon, #540 430).

The concentrated Hb solution can then be directed into one or more parallel chromatographic columns to further separate the hemoglobin by high performance liquid chromatography from other contaminants such as antibodies, endotoxins, phospholipids and enzymes and viruses. Examples of suitable media include anion exchange media, cation exchange media, hydrophobic interaction media and affinity media. In a preferred embodiment, chromatographic columns contain an anion exchange medium suitable to separate Hb from non-hemoglobin proteins. Suitable anion exchange mediums include, for example, silica, alumina, titania gel, cross-linked dextran, agarose or a derivatized moiety, such as a polyacrylamide, a polyhydroxyethylmethacrylate or a styrene divinylbenzene, that has been derivatized with a cationic chemical functionality, such as a diethylamino ethyl or quaternary aminoethyl group. A suitable anion exchange medium and corresponding eluants for the selective absorption and desorption of Hb as compared to other proteins and contaminants, which are likely to be in a lysed RBC phase, are readily determinable by one of reasonable skill in the art.

In a more preferred embodiment, a method is used to form an anion exchange media from silica gel, which is hydrothermally treated to increase the pore size, exposed to γ-glycidoxy propylsilane to form active epoxide groups and then exposed to $C_3H_7(CH_3)NCl$ to form a quaternary ammonium anion exchange medium. This method is described in the *Journal of Chromatography*, 120:321–333 (1976), which is incorporated herein by reference in its entirety.

Chromatographic columns are first pre-treated by flushing with a first eluant which facilitates Hb binding. Concentrated Hb solution is then injected onto the medium in the columns. After injecting the concentrated Hb solution, the chromatographic columns are then successively washed with different eluants to produce a separate, purified Hb eluate.

In a preferred embodiment, a pH gradient is used in chromatographic columns to separate protein contaminants, such as the enzyme carbonic anhydrase, phospholipids, antibodies and endotoxins from the Hb. Each of a series of buffers having different pH values, are sequentially directed to create a pH gradient within the medium in the chromatographic column. It is preferred that the buffers be filtered, such as with a 10,000 Dalton depyrogenation membrane. The buffers used to separate Hb should have a low ionic strength such that elution of Hb and non-hemoglobin contaminants is generally dependent upon pH and not significantly dependent upon ionic strength. Typically, buffers with an ionic concentration of about 50 mM, or less, have suitable low ionic strengths.

The first buffer transports the concentrated Hb solution into the medium in the chromatographic columns and facilitates binding of the Hb to the medium. The second buffer then adjusts the pH within the columns to elute contaminating non-hemoglobin components while maintaining the Hb bound to the medium. The third buffer then elutes the Hb. The Hb eluate is then collected. It is preferred that the Hb eluate be directed through a sterile filter. Suitable sterile filters include 0.22 μM filters, such as a Sartorius Sartobran Cat#5232507 G1PH filter.

In a preferred embodiment, the first 3%-to-4% of the Hb eluate and the last 3%-to-4% of the Hb, eluate are directed to waste to provide assurance of the purity of the Hb eluate.

Wherein the chromatographic columns are to be reused, contaminating non-hemoglobin proteins and endotoxin, remaining in the columns, are then eluted by a fourth buffer.

The use of pH gradients to separate Hb form non-hemoglobin contaminants is further described in U.S. Pat. No. 5,691,452, filed Jun. 7, 1995, which are incorporated herein by reference.

In a preferred embodiment, the first buffer is a tris-hydroxymethyl aminomethane (Tris) solution (concentration about 20 mM; pH about 8.4 to about 9.4). The second buffer is a mixture of the first buffer and a third buffer, with the second buffer having a pH of about 8.2 to about 8.6. The third buffer is a Tris solution (concentration about 50 mM; pH about 6.5 to about 7.5). The fourth buffer is a NaCl/Tris solution (concentrations about 1.0 M NaCl and about 20 mM Tris; pH about 8.4 to about 9.4, preferably about 8.9–9.1). It is particularly preferred that the pH of the second buffer be between about 8.2 and about 8.4.

Typically, the buffers used are at a temperature between about 0° C. and about 50° C. Preferably, buffer temperature is about 12.4±1.0° C. during use. In addition, the buffers are typically stored at a temperature of about 9° C. to about 11° C.

The Hb eluate is then preferably deoxygenated prior to polymerization to form a deoxygenated Hb solution (hereinafter deoxy-Hb) by means that substantially deoxygenate the Hb without significantly reducing the ability of the Hb in the Hb eluate to transport and release oxygen, such as would occur from denaturation of formation of oxidized hemoglobin (metHb).

In one embodiment, the Hb eluate is deoxygenated by gas transfer of an inert gas across a phase membrane. Such inert gases include, for example, nitrogen, argon and helium. It is understood that other means for deoxygenating a solution of hemoglobin, which are known in the art, can be used to deoxygenate the Hb eluate. Such other means, can include, for example, nitrogen sparging of the Hb eluate, chemical scavenging with reducing agents such as N-acetyl-L-cysteine (NAC), cysteine, sodium dithionite or ascorbate, or photolysis by light.

Following elution from the chromatographic column, the Hb eluate is preferably concentrated to improve the efficiency of the process. The Hb eluate is recirculated through an ultrafilter to concentrate the Hb eluate to form a concentrated Hb solution. Suitable ultrafilters include, for example, 30,000 or less Dalton ultrafilters (e.g., Millipore Helicon, Cat# CDUTF050G1 or Amicon Cat# 540430). Typically, concentration of the Hb eluate is complete when the concentration of Hb is between about 100 to about 120 g/l. While concentrating the Hb eluate, the Hb eluate temperature is preferably maintained at approximately 8–12° C.

Buffer is then directed into the Hb solution, which is preferably concentrated, to adjust the ionic strength of the Hb solution to enhance Hb deoxygenation. It is preferred that the ionic strength be adjusted to between about 150 meq/l and about 200 meq/l to reduce the oxygen affinity of the Hb in the Hb solution. Suitable buffers include buffers with a pH that will not result in significant denaturing of the Hb protein but will have an ionic strength sufficiently high to promote Hb deoxygenation. Examples of suitable buffers include saline solutions with a pH range of about 6.5 to about 8.9. A preferred buffer is an aqueous 1.0 M NaCl, 20 mM Tris solution with a pH of about 8.9.

Preferably, the resulting buffered Hb solution is then recirculated through the ultrafilter, to again concentrate the Hb solution to improve the efficiency of the process. In a preferred embodiment, concentration is complete when the concentration of Hb is about 100 g/l to about 120 g/l.

During deoxygenation the Hb solution is circulated through a suitable phase transfer membrane. Appropriate phase transfer membranes include, for example, a 0.05 μm polypropylene hollow fiber microfilter (e.g., Hoechst-Celanese Cat# 5PCM-107). Concurrently, a counterflow of an inert gas is passed across the phase transfer membrane. Suitable inert gases include, for example, nitrogen, argon and helium. Gas exchange across the phase transfer membrane thereby strips oxygen out of the Hb solution.

Deoxygenation continues until the $pO_2$ of the Hb solution is reduced to a level wherein the oxygenated Hb (oxyhemoglobin or $HbO_2$) content in the Hb solution is about 20% or less. In a preferred embodiment, the $HbO_2$ content in the Hb solution is about 10% or less.

During deoxygenation, the temperature of the Hb solution is typically maintained at a level that will balance the rate of deoxygenation against the rate of methemoglobin formation. Temperature is maintained to limit methemoglobin content to less than 20%. An optimum temperature will result in less than about 5% methemoglobin content, and preferably less than about 2.5% methemoglobin content, while still deoxygenating the Hb solution. Typically, during deoxygenation the temperature of the Hb solution is maintained between about 19° C. and about 31° C.

During deoxygenation, and subsequently throughout the remaining steps of the method of invention, the Hb is maintained in a low oxygen environment to minimize oxygen absorption by the Hb and to maintain an $HbO_2$ content of less than about 20%, preferably less than about 10%.

The deoxygenated-Hb is then preferably equilibrated with a low oxygen content storage buffer, containing a sulfhydryl compound, to form an oxidation-stabilized deoxy-Hb. Suitable sulfhydryl compounds include non-toxic reducing agents, such as N-acetyl-L-cysteine (NAC) D,L-cysteine, γ-glutamyl-cysteine, glutathione, 2,3-dimercapto-1-propanol, 1,4-butanedithiol, thioglycolate, and other biologically compatible sulfhydryl compounds. The oxygen content of a low oxygen content storage buffer must be low enough not to significantly reduce the concentration of sulfhydryl compound in the buffer and to limit oxyhemoglobin content in oxidation stabilized deoxy-Hb to about 20% or less, preferably less than about 10%. Typically, the storage buffer has a $pO^2$ of less than about 50 torr.

In a preferred embodiment, the storage buffer should have a pH suitable to balance Hb polymerization and methemoglobin formation, typically between about 7.6 and about 7.9.

The amount of a sulfhydryl compound mixed with the deoxy-Hb is an amount high enough to increase intramolecular cross-linking of Hb during polymerization and low enough not to significantly decrease intermolecular cross-linking of Hb molecules, due to a high ionic strength. Typically, about one mole of sulfhydryl functional groups (-SH) are needed to oxidation stabilize between about 0.25 moles to about 5 moles of deoxy-Hb.

In a preferred embodiment, the storage buffer contains approximately 25–35 mM sodium phosphate buffer (pH 7.7–7.8) and contains an amount of NAC such that the concentration of NAC in oxidation stabilized deoxy-Hb is between about 0.003% and about 0.3%, by weight. More preferably, the NAC concentration in the oxidation stabilized deoxy-Hb is between about 0.05% and about 0.2% by weight.

Preferably, the storage buffer is filtered prior to mixing with the deoxy-Hb, such as through a 10,000 Dalton ultrafiltration membrane (Millipore Helicon Cat# CDUF050G1 or A/G Technology Maxcell Cat#UFP-10-C-75).

In one embodiment, the oxidation-stabilized deoxy-Hb then flows through an optional filter. Suitable filters include a 0.2 μm polypropylene prefilter and a 0.5 μm sterile microfilter (Pall Profile II, Cat#ABIY005Z7 or Gelman Supor). The deoxy-Hb is maintained under a substantially oxygen-free atmosphere. This can be accomplished, for example, by purging and blanketing the process apparatus with an inert gas, such as nitrogen, prior to and after filling with oxidation-stabilized deoxy-Hb.

Optionally, prior to transferring the oxidation-stabilized deoxy-Hb to Polymerization, an appropriate amount of water is added to the polymerization reactor. In one embodiment an appropriate amount of water is that amount which would result in a solution with a concentration of about 10 to about 100 g/l Hb when the oxidation-stabilized deoxy-Hb is added to the polymerization reactor. Preferably, the water is oxygen-depleted.

After the $pO_2$ of the water in the polymerization step is reduced to a level sufficient to limit $HbO_2$ content to about 20%, typically less than about 50 torr, the polymerization reactor is blanketed with an inert gas, such as nitrogen. The oxidation-stabilized deoxy-Hb is then transferred into the polymerization reactor, which is concurrently blanketed with an appropriate flow of an inert gas.

The temperature of the oxidation-stabilized deoxy-Hb solution in polymerization reactor is raised to a temperature to optimize polymerization of the oxidation-stabilized deoxy-Hb when contacted with a cross-linking agent. Typically, the temperature of the oxidation-stabilized deoxy-Hb is about 25° C. to about 45° C., and preferably about 41° C. to about 43° C. throughout polymerization. An example of an acceptable heat transfer means for heating the polymerization reactor is a jacketed heating system which is heated by directing hot ethylene glycol through the jacket.

The oxidation-stabilized deoxy-Hb is then exposed to a suitable cross-linking agent at a temperature sufficient to polymerize the oxidation-stabilized deoxy-Hb to form a solution of polymerized hemoglobin (poly(Hb)) over a period of about 2 hours to about 6 hours.

Examples of suitable cross-linking agents include polyfunctional agents that will cross-link Hb proteins, such as glutaraldehyde, succindialdehyde, activated forms of polyoxyethylene and dextran, α-hydroxy aldehydes, such as glycolaldehyde, N-maleimido-6-aminocaproyl-(2'-nitro,4'-sulfonic acid)-phenyl ester, m-maleimidobenzoic acid-N-hydroxysuccinimide ester, succinimidyl 4-(N-maleimidomethyl)cyclohexane-1-carboxylate, sulfosuccinimidyl 4-(N-maleimidomethyl)cyclohexane-1-carboxylate, m-maleimidobenzoyl-N-hydroxysuccinimide ester, m-maleimidobenzoyl-N-hydroxysulfosuccinimide ester, N-succinimidyl(4-iodoacetyl)aminobenzoate, sulfosuccinimidyl(4-iodoacetyl)aminobenzoate, succinimidyl 4-(p-maleimidophenyl)butyrate, sulfosuccinimidyl 4-(p-maleimidophenyl)butyrate, 1-ethyl-3-(3-dimethylaminopropyl)carbodiimide hydrochloride, N,N'-phenylene dimaleimide, and compounds belonging to the bis-imidate class, the acyl diazide class or the aryl dihalide class, among others.

A suitable amount of a cross-linking agent is that amount which will permit intramolecular cross-linking to stabilize the Hb and also intermolecular cross-linking to form polymers of Hb, to thereby increase intravascular retention. Typically, a suitable amount of a cross-linking agent is that amount wherein the molar ratio of cross-linking agent to Hb is in excess of about 2:1. Preferably, the molar ratio of cross-linking agent to Hb is between about 20:1 to 40:1.

Preferably, the polymerization is performed in a buffer with a pH between about 7.6 to about 7.9, having a chloride concentration less than or equal to about 35 mmolar.

In a preferred embodiment, a suitable amount of the cross-linking agent is added to the oxidation-stabilized deoxy-Hb and then mixed by a means for mixing with low shear. A suitable low-shear mixing means includes a static mixer. A suitable static mixer is, for example, a "Kenics" static mixer obtained from Chemineer, Inc.

In one embodiment, recirculating the oxidation-stabilized deoxy-Hb and the cross-linking agent through the static mixer causes turbulent flow conditions with generally uniform mixing of the cross-linking, agent with the oxidation-stabilized deoxy-Hb thereby reducing the potential for forming pockets of deoxy-Hb containing high concentrations of the cross-linking agent. Generally uniform mixing of the cross-linking agent and the deoxy-Hb reduces the formation of high molecular weight Hb polymers, i.e. polymers weighing more than 500,000 Daltons, and also permits faster mixing of the cross-linking agent and the deoxy-Hb during polymerization. Furthermore, significant Hb intramolecular cross-linking will result during Hb polymerization due to the presence of a sulfhydryl compound, preferably NAC. While the exact mechanism of the interaction of the sulfhydryl compound with glutaraldehyde and/or Hb is not known, it is presumed that the sulfhydryl compound affects Hb/cross-linking agent chemical bonding in a manner that at least partially inhibits the formation of high molecular weight Hb polymers and preferentially forms stabilized tetrameric Hb.

Poly(Hb) is defined as having significant intramolecular cross-linking if a substantial portion (e.g., at least about 50%) of the Hb molecules are chemically bound in the poly(Hb), and only a small amount, such as less than about 15% are contained within high molecular weight polymerized hemoglobin chains. High molecular weight poly(Hb) molecules are molecules, for example, with a molecular weight above about 500,000 Daltons.

In a preferred embodiment, glutaraldehyde is used as the cross-linking agent. Typically, about 10 to about 70 grains of glutaraldehyde are used per kilogram of oxidation-stabilized deoxy-Hb. More preferably, glutaraldehyde is added over a period of five hours until approximately 29–31 grams of glutaraldehyde are added for each kilogram of oxidation-stabilized deoxy-Hb.

After polymerization, the temperature of the poly(Hb) solution in polymerization reactor is typically reduced to about 15° C. to about 25° C.

Wherein the cross-linking agent used is not an aldehyde, the poly(Hb) formed is generally a stable poly(Hb). Wherein the cross-linking agent used is an aldehyde, the poly(Hb) formed is generally not stable until mixed with a suitable reducing agent to reduce less stable bonds in the poly(Hb) to form more stable bonds. Examples of suitable reducing agents include sodium borohydride, sodium cyanoborohydride, sodium dithionite, trimethylamine, t-butylamine, morpholine borane and pyridine borane. Prior to adding the reducing agent, the poly(Hb) solution is optionally concentrated by ultrafiltration until the concentration of the poly(Hb) solution is increased to between about 75 and about 85 g/l. An example of a suitable ultrafilter is a 30,000 Dalton filter (e.g., Millipore Helicon, Cat# CDUF050LT and Amicon, Cat# 540430).

The pH of the poly(Hb) solution is then adjusted to the alkaline pH range to preserve the reducing agent and to prevent hydrogen gas formation, which can denature Hb during the subsequent reduction. In one embodiment, the pH is adjusted to greater than 10. The pH can be adjusted by adding a buffer solution to the poly(Hb) solution during or after polymerization. The poly(Hb) is typically purified to remove non-polymerized hemoglobin. This can be accomplished by dialfiltration or hydroxyapatite chromatography (see, e.g. U.S. Pat. No. 5,691,453, which is incorporated herein by reference).

Following pH adjustment, at least one reducing agent, preferably a sodium borohydride solution, is added to the polymerization step typically through the deoxygenation loop. Typically, about 5 to about 18 moles of reducing agent are added per mole of Hb tetramer (per 64,000 Daltons of Hb) within the poly(Hb). In a preferred embodiment, for every nine liters of poly(Hb) solution in polymerization subsystem 98, one liter of 0.25 M sodium borohydride solution is added at a rate of 0.1 to 0.12 lpm.

The pH and electrolytes of the stable poly(Hb) can then be restored to physiologic levels to form a stable polymerized hemoglobin blood-substitute, by diafiltering the stable poly(Hb) with a diafiltration solution having, a suitable pH and physiologic electrolyte levels. Preferably, the diafiltration solution is a buffer solution.

Wherein the poly(Hb) was reduced by a reducing agent, the diafiltration solution has an acidic pH, preferably between about 4 to about 6.

A non-toxic sulfhydryl compound can also be added to the stable poly(Hb) solution as an oxygen scavenger to enhance the stability of the final polymerized hemoglobin blood-substitute. The sulfhydryl compound can be added as part of the diafiltration solution and/or can be added separately. An amount of sulfhydryl compound is added to establish a sulfhydryl concentration which will scavenge oxygen to maintain methemoglobin content less than about 15% over the storage period. Preferably, the sulfhydryl compound is NAC. Typically, the amount of sulfhydryl compound added is an amount sufficient to establish a sulfhydryl concentration between about 0.05% and about 0.2% by weight.

In a preferred embodiment, the blood-substitute is packaged under aseptic handling conditions while maintaining pressure with an inert, substantially oxygen-free atmosphere, in the polymerization reactor and remaining transport apparatus.

The specifications for a suitable stable polymerized hemoglobin blood-substitute formed by the method of invention are provided in Table I.

TABLE I

| PARAMETER | RESULTS |
| --- | --- |
| pH (18–22° C.) | Physiologically acceptable |
| Endotoxin | Physiologically acceptable |
| Sterility Test | Meets Test |
| Phospholipids[a] | Physiologically acceptable |
| Total Hemoglobin | 10–250 g/l |
| Methemoglobin | <15% |
| Oxyhemoglobin | <10% |
| Sodium, $Na^+$ | Physiologically acceptable |
| Potassium, $K^+$ | |
| Chloride, $Cl^-$ | |
| Calcium, $Ca^{++}$ | |
| Boron | |
| Glutaraldehyde | Physiologically acceptable |
| N-acetyl-L-cysteine | Physiologically acceptable |
| M.W. >500,000 | ≦15% |
| M.W. ≦65,000 | <10% |
| M.W. <32,000 | <5% |
| Particulate Content >10μ | <12/ml |
| Particulate Content >25μ | <2/ml |

[a]measured in Hb before polymerization

The stable blood-substitute is then stored in a short-term storage container or into sterile storage containers, each having a low oxygen environment as described in detail above. The storage container should also be sufficiently impermeable to water vapor passage to prevent significant concentration of the blood-substitute by evaporation over the storage period. Significant concentration of the blood-substitute is concentration resulting in one or more parameters of the blood-substitute being high out of specification.

The synthesis of a stable polymerized hemoglobin blood-substitute, formed according to the method of invention, is further described in U.S. Pat. No. 5,296,465.

Vertebrates which can receive the blood-substitute, formed by the methods of the invention include mammals, such as a human, non-human primate, a dog, a cat, a rat, a horse or a sheep. Further, vertebrates, which can receive said blood-substitute, includes fetuses (prenatal vertebrate), post-natal vertebrates, or vertebrates at time of birth.

A blood-substitute of the present invention can be administered into the circulatory system by injecting the blood-substitute directly and/or indirectly into the circulatory system of the vertebrate, by one or more injection methods. Examples of direct injection methods include intravascular injections, such as intravenous and intra-arterial injections, and intracardiac injections. Examples of indirect injection methods include intraperitoneal injections, subcutaneous injections, such that the blood-substitute will be transported by the lymph system into the circulatory system or injections into the bone marrow by means of a trocar or catheter. Preferably, the blood-substitute is administered intravenously.

The vertebrate being treated can be normovolemic, hypervolemic or hypovolemic prior to, during, and/or after infusion of the blood-substitute. The blood-substitute can be directed into the circulatory system by methods such as top loading and by exchange methods.

A blood-substitute can be administered therapeutically, to treat hypoxic tissue within a vertebrate resulting from many different causes including reduced RBC flow in a portion of, or throughout, the circulatory system, anemia and shock. Further, the blood-substitute can be administered prophylactically to prevent oxygen-depletion of tissue within a vertebrate, which could result from a possible or expected reduction in RBC flow to a tissue or throughout the circulatory system of the vertebrate. Further discussion of the administration of hemoglobin to therapeutically or prophylactically treat hypoxia, particularly from a partial arterial obstruction or from a partial blockage in microcirculation, and the dosages used therein, is provided in copending U.S. patent application Ser. No. 08/409,337, filed Mar. 23, 1995, which is incorporated herein by reference in its entirety.

Typically, a suitable dose, or combination of doses of blood-substitute, is an amount which when contained within the blood plasma will result in a total hemoglobin concentration in the vertebrate's blood between about 0.1 to about 10 grams Hb/dl, or more, if required to make up for large volume blood losses.

The invention will now be further and specifically described by the following examples.

EXAMPLE 1

Synthesis of Stable Polymerized Hb Blood-Substitute

As described in U.S. Pat. No. 5,296,465, samples of bovine whole blood were collected, mixed with a sodium citrate anticoagulant to form a blood solution.

Each blood solution sample was maintained after collection at a temperature of about 2° C. and then strained to remove large aggregates and particles with a 600 mesh screen.

Prior to pooling, the penicillin level in each blood solution sample was assayed with an assay kit purchased from Difco, Detroit, Mich. using the method entitled "Rapid Detection of Penicillin in Milk" to ensure that penicillin levels in the blood solutions were <0.008 units/ml.

The blood solution samples were then pooled and mixed with depyrogenated aqueous sodium citrate solution to form a 0.2% by weight solution of sodium citrate in bovine whole blood (hereafter "0.2% sodium citrate blood solution").

The 0.2% sodium citrate blood solution was then passed, in-series, through 800 µm and 50 µm polypropylene filters to remove large blood solution debris of a diameter approximately 50 µm or more.

The RBCs were then washed to separate extracellular plasma proteins, such as BSA or IgG, from the RBCs. To wash the RBCs contained in the blood solution, the volume of blood solution in the diafiltration tank was initially diluted by the addition of an equal volume of a filtered isotonic solution to diafiltration tank. The isotonic solution was filtered with a Millipore (Cat# CDUF 050 G1) 10,000 Dalton ultrafiltration membrane. The isotonic solution was composed of 6.0 g/l sodium citrate dihydrate and 8.0 g/l sodium chloride in water-for-injection (WFI).

The diluted blood solution was then concentrated back to its original volume by diafiltration through a 0.2 µm hollow fiber (Microgon Krosflo II microfiltration cartridge) diafilter. Concurrently, filtered isotonic solution was added continuously, as makeup, at a rate equal to the rate of filtrate loss through the 0.2 µm diafilter. During diafiltration, components of the diluted blood solution which were significantly smaller in diameter than RBCs, or are fluids such as plasma, passed through the walls of the 0.2 µm diafilter with the filtrate. RBCs, platelets and larger bodies of the diluted blood solution, such as white blood cells, were retained with continuously-added isotonic solution to form a dialyzed blood solution.

During RBC washing, the diluted blood solution was maintained at a temperature between approximately 10 to 25° C. with a fluid pressure at the inlet of the diafilter between about 25 psi and about 30 psi to improve process efficiency.

RBC washing was complete when the volume of filtrate drained from the diafilter equaled about 600% of the volume of blood solution prior to diluting with filtered isotonic solution.

The dialyzed blood solution was then continuously pumped at a rate of approximately 4 lpm to a Sharples Super Centrifuge, Model #AS-16, fitted with a #28 ringdam. The centrifuge was operating while concurrently being fed dialyzed blood solution, to separate the RBCs from the white blood cells and platelets. During operation, the centrifuge rotated at a rate sufficient to separate the RBCs into a heavy RBC phase, while also separating a substantial portion of the white blood cells (WBCs) and platelets into a light WBC phase, specifically about 15,000 rpm. A fraction of the RBC phase and of the WBC phase were separately and continuously discharged from the centrifuge during operation.

Following, separation of the RBCs, the RBCs were lysed to form a hemoglobin-containing solution. A substantial portion of the RBCs were mechanically lysed while discharging the RBCs from the centrifuge. The cell membranes of the RBCs ruptured upon impacting the wall of RBC phase discharge line at an angle to the flow of RBC phase out of the centrifuge, thereby releasing hemoglobin (Hb) from the RBCs into the RBC phase.

The lysed RBC phase then flowed through the RBC phase discharge line into a static mixer (Kenics ½ inch with 6 elements, Chemineer, Inc.). Concurrent with the transfer of the RBC phase to the static mixer, an equal amount of WFI was also injected into the static mixer, wherein the WFI mixed with the RBC phase. The flow rates of the RBC phase and the WFI into the static mixer are each at about 0.25 lpm.

Mixing the RBC phase with WFI in the static mixer produced a lysed RBC colloid. The lysed RBC colloid was then transferred from the static mixer into a Sharples Super Centrifuge (Model #AS-16, Sharples Division of Alfa-Laval Separation, Inc.) which was suitable to separate the Hb from non-hemoglobin RBC components. The centrifuge was rotated at a rate sufficient to separate the lysed RBC colloid into a light Hb phase and a heavy phase. The light phase was composed of Hb and also contained non-hemoglobin components with a density approximately equal to or less than the density of Hb.

The Hb phase was continuously discharged from the centrifuge, through a 0.45 µm Millipore Pellicon Cassette, Cat#HVLP 000 C5 micro filter, and into a holding tank in preparation for Hb purification. Cell stroma were then returned with the retentate from the microfilter to the holding tank. During microfiltration, the temperature within the holding tank was maintained at 10° C. or less. To improve efficiency, when the fluid pressure at the microfilter inlet increased from an initial pressure of about 10 psi to about 25 psi, microfiltration was complete. The Hb microfiltrate was then transferred from the microfilter into the microfiltrate tank.

Subsequently, the Hb microfiltrate was pumped through a 100,000 Millipore Cat# CDUF 050 HI ultrafilter. A substantial portion of the Hb and water, contained in the Hb microfiltrate, permeated the 100,000 Dalton ultrafilter to form a Hb ultrafiltrate, while larger cell debris, such as proteins with a molecular weight above about 100,000 Dalton, were retained and recirculated back into the microfiltrate tank. Concurrently, WFI was continuously added to the microfiltrate tank as makeup for water lost in the ultrafiltrate. Generally, cell debris include all whole and fragmented cellular components with the exception of Hb, smaller cell proteins, electrolytes, coenzymes and organic metabolic intermediates. Ultrafiltration continued until the concentration of Hb in the microfiltrate tank was less than 8 grams/liter (g/l). While ultrafiltering the Hb, the internal temperature of the microfiltrate tank was maintained at about 10° C.

The Hb ultrafiltrate was transferred into an ultrafiltrate tank, wherein the Hb ultrafiltrate was then recirculated through a 30,000 Dalton Millipore Cat# CDUF 050 T1 ultrafilter to remove smaller cell components, such as electrolytes, coenzymes, metabolic intermediates and proteins less than about 30,000 Daltons in molecular weight, and water from the Hb ultrafiltrate, thereby forming a concentrated Hb solution containing about 100 g Hb/l.

The concentrated Hb solution was then directed from the ultrafiltrate tank onto the media contained in parallel chromatographic columns (2 feet long with an 8 inch inner diameter) to separate the Hb by high performance liquid chromatography. The chromatographic columns contained an anion exchange medium suitable to separate Hb from nonhemoglobin proteins. The anion exchange media was formed from silica gel. The silica gel was exposed to γ-glycidoxy propylsilane to form active epoxide groups and then exposed to $C_3H_7(CH_3)NCl$ to form a quaternary ammonium anion exchange medium. This method of treating silica gel is described in the *Journal of Chromatography*, 120: 321–333 (1976).

Each column was pre-treated by flushing, the chromatographic columns with a first buffer which facilitated Hb binding. Then 4.52 liters of the concentrated Hb solution were injected into each chromatographic column. After injecting the concentrated Hb solution, the chromatographic columns were then washed by successively directing three different buffers through the chromatographic columns to produce a Hb eluate, by producing a pH gradient within the columns. The temperature of each buffer during, use was about 12.4° C. The buffers were prefiltered through a 10,000 Dalton ultrafiltration membrane before injection onto the chromatographic columns.

The first buffer, 20 mM tris-hydroxymethyl aminomethane (Tris) (pH about 8.4 to about 9.4), transported the concentrated Hb, solution into the media in the chromatographic columns to bind the Hb. The second buffer, a mixture of the first buffer and a third buffer, with the second buffer having a pH of about 8.3, then adjusted the pH within chromatographic columns to elute contaminating non-hemoglobin components from the chromatographic columns, while retaining the Hb. Equilibration with the second buffer continued for about 30 minutes at a flow rate of approximately 3.56 lpm per column. The elute from the second buffer was discarded to waste. The third buffer, 50 mM Tris (pH about 6.5 to about 7.5), then eluted the Hb from the chromatographic columns.

The Hb eluate was then directed through a sterile 0.22μ Sartobran Cat# 5232507 G1PH filter to a tank wherein the Hb eluate was collected. The first 3-to-4% of the Hb eluate and the last 3-to-4% of the Hb eluate were directed to waste.

The Hb eluate was further used if the eluate contained less than 0.05 EU/ml of endotoxin and contained less than 3.3 mmoles/ml phospholipids. To sixty liters of ultrapure eluate, which had a concentration of 100 g Hb/l, was added 91 of 1.0 M NaCl, 20 mM Tris (pH 8.9) buffer, thereby forming a Hb solution with an ionic strength of 160 mM, to reduce the oxygen affinity of the Hb in the Hb solution. The Hb solution was then concentrated at 10° C., by recirculating through the ultrafilter, specifically a 10,000 Dalton Millipore Helicon, Cat#CDUF050G1 filter, until the Hb concentration was 110 g/l.

The Hb solution was then deoxygenated, until the $pO_2$ of the Hb solution was reduced to the level where $HbO_2$ content was about 10%, by recirculating the Hb solution at 12 lpm, through a 0.05 μm Hoechst-Celanese Corporation Cat# G-240/40) polypropylene microfilter phase transfer membrane, to form a deoxygenated Hb solution (hereinafter "deoxy-Hb"). Concurrently, a 60 lpm flow of nitrogen gas was directed through the counter side of the phase transfer membrane. During deoxygenation, the temperature of the Hb solution was maintained between about 19° C. and about 31° C.

Also during deoxygenation, and subsequently throughout the process, the Hb was maintained in a low oxygen environment to minimize oxygen absorption by the Hb and to maintain an oxygenated Hb (oxyhemoglobin or $HbO_2$) content of less than about 10% in the deoxy-Hb.

The deoxy-Hb, 60 liters) was then diafiltered through an ultrafilter with 180 l of a storage buffer, containing 0.2 wt % N-acetyl cysteine, 33 mM sodium phosphate buffer (pH 7.8) having a $pO_2$ of less than 50 torr, to form a oxidation-stabilized deoxy-Hb. Prior to mixing with the deoxy-Hb, the storage buffer was depyrogenated with a 10,000 Dalton Millipore Helicon, Cat#CDUF050G1 depyrogenating filter.

The storage buffer was continuously added at a rate approximately equivalent to the fluid loss across the ultrafilter. Diafiltration continued until the volume of fluid lost through diafiltration across the ultrafilter was about three times the initial volume of the deoxy-Hb.

Prior to transferring the oxidation-stabilized deoxy-Hb into a polymerization apparatus, oxygen-depleted WFI was added to the polymerization reactor to purge the polymerization apparatus of oxygen to prevent oxygenation of oxidation-stabilized deoxy-Hb. The amount of WFI added to the polymerization apparatus was that amount which would result in a Hb solution with a concentration of about 40 g Hb/l, when the oxidation-stabilized deoxy-Hb was added to the polymerization reactor. The WFI was then recirculated throughout the polymerization apparatus, to deoxygenate the WFI by flow through a 0.05 μm polypropylene microfilter phase transfer membrane (Hoechst-Celanese Corporation Cat#5PCM-108, 80 sq. ft.) against a counterflow of pressurized nitrogen. The flow rates of WFI and nitrogen gas, through the phase transfer membrane, were about 18 to 20 lpm and 40 to 60 lpm, respectively.

After the $pO_2$ of the WFI in the polymerization apparatus was reduced to less than about 2 torr $pO_2$, the polymerization reactor was blanketed with nitrogen by a flow of about 20 lpm of nitrogen into the head space of the polymerization reactor.

The oxidation-stabilized deoxy-Hb was then transferred into the polymerization reactor.

The polymerization was conducted in a 12 mM phosphate buffer with a pH of 7.8, having a chloride concentration less than or equal to about 35 mmolar.

The oxidation-stabilized deoxy-Hb and N-acetyl cysteine were subsequently slowly mixed with the cross-linking agent glutaraldehyde, specifically 29.4 grams of glutaraldehyde for each kilogram of Hb over a five hour period, while heating at 40° C. and recirculating the Hb solution through a Kenics 1-1/inch static mixer with 6 elements (Chemineer, Inc.), to form a polymerized Hb (poly(Hb)) solution.

Recirculating the oxidation-stabilized deoxy-Hb and the glutaraldehyde through the static mixer caused turbulent flow conditions with generally uniform mixing of the glutaraldehyde with the oxidation-stabilized deoxy-Hb, thereby reducing the potential for forming pockets of deoxy-Hb containing high concentrations of glutaraldehyde. Generally uniform mixing of glutaraldehyde and deoxy-Hb reduced the formation of high molecular weight poly(Hb) (having a molecular weight above 500,000 Daltons) and also permitted faster mixing of glutaraldehyde and deoxy-Hb during polymerization.

In addition, significant Hb, intramolecular cross-linking resulted during Hb polymerization as an effect of the presence of N-acetyl cysteine upon the polymerization of Hb.

After polymerization, the temperature of the poly(Hb) solution in the polymerization reactor was reduced to a temperature between about 15° C. to about 25° C.

The poly(Hb) solution was then concentrated by recirculating the poly(Hb) solution through the ultrafilter until the concentration of the poly(Hb) was increased to about 85 g/l. A suitable ultrafilter is a 30,000 Dalton filter (e.g., Millipore Helicon, Cat#CDUF050LT).

Subsequently, the poly(Hb) solution was then mixed with 66.75 g sodium borohydride and again recirculated through the static mixer. Specifically, for every nine liters of poly (Hb) solution, one liter of 0.25 M sodium borohydride solution was added at a rate of 0.1 to 0.12 lpm.

Prior to adding the sodium borohydride to the poly(Hb) solution, the pH of the poly(Hb) solution was basified by adjusting pH to a pH of about 10 to preserve the sodium borohydride and to prevent hydrogen gas formation. The pH of the poly(Hb) solution was adjusted by diafiltering the poly(Hb) solution with approximately 215l of depyrogenated, deoxygenated 12 mM sodium borate buffer, having a pH of about 10.4 to about 10.6. The poly(Hb) solution was diafiltered by recirculating the poly(Hb) solution from the polymerization reactor through the 30 kD ultrafilter. The sodium borate buffer was added to the poly(Hb) solution at a rate approximately equivalent to the rate of fluid loss across the ultrafilter from diafiltration. Diafiltration continued until the volume of fluid lost across the ultrafilter from diafiltration was about three times the initial volume of the poly(Hb) solution in the polymerization reactor.

Following pH adjustment, sodium borohydride solution was added to the polymerization reactor to reduce bonds in the poly(Hb) solution to bonds and to form stable poly(Hb) in solution. During the sodium borohydride addition, the poly(Hb) solution in the polymerization reactor was continuously recirculated through the static mixer and the 0.05 μm polypropylene microfilter phase transfer membrane to remove dissolved oxygen and hydrogen. Flow through a static mixer also provided turbulent sodium borohydride flow conditions that rapidly and effectively mixed sodium borohydride with the poly(Hb) solution. The flow rates of poly(Hb) solution and nitrogen gas through the 0.05 lpm phase transfer membrane were between about 2.0 to 4.0 lpm and about 12 to 18 lpm, respectively. After completion of the sodium borohydride addition, reduction continued in the polymerization reactor while an agitator contained therein rotated at approximately 75 rotations per minute.

Approximately one hour after the sodium borohydride addition, the stable poly(Hb) solution was recirculated from the polymerization reactor through the 30,000 Dalton ultrafilter until the stable poly(Hb) solution concentration was 110 g/l. Following concentration, the pH and electrolytes of the stable poly(Hb) solution were restored to physiologic levels to form a stable polymerized Hb blood-substitute, by diafiltering the stable poly(Hb) solution, through the 30,000 Dalton ultrafilter, with a filtered, deoxygenated, low pH buffer containing 27 mM sodium lactate, 12 mM NAC, 115 mM NaCl, 4 mM KCl, and 1.36 mM $CaCl_2$ in WFI, (pH 5.0). Diafiltration continued until the volume of fluid lost through diafiltration across the ultrafilter was about 6 times the pre-diafiltration volume of the concentrated Hb product.

After the pH and electrolytes were restored to physiologic levels, the stable polymerized Hb blood-substitute was then diluted to a concentration of 5.0 g/dl by 25, adding the filtered, deoxygenated low pH buffer to the polymerization reactor. The diluted blood-substitute was then diafiltered by recirculating from the polymerization reactor through the static mixer and a 100,000 Dalton purification filter against a filtered deoxygenated buffer containing 27 mM sodium lactate, 12 mm NAC, 115 mM NaCl, 4 mM KCl, and 1.36 mM $CaCl_2$ in WFI, (pH 7.8). Diafiltration continued until the blood-substitute contained less than or equal to about 10% modified tetrameric and unmodified tetrameric species by GPC when run under dissociating conditions.

The purification filter was run under conditions of low transmembrane pressure with a restricted permeate line. Following removal of substantial amounts of modified tetrameric Hb and unmodified tetrameric Hb, recirculation of the blood-substitute continued through the 30,000 Dalton ultrafilter until the concentration of the blood-substitute was about 130 g/l.

The stable blood-substitute was then stored in a suitable container having a low oxygen environment and a low oxygen in-leakage.

EXAMPLE 2

Hemoglobin Blood-Substitute Storage: Foil Overwrap

The hemoglobin blood-substitute, as prepared in Example 1, packaged in a 600 mL Stericon package, was overwrapped in a foil laminate package (KAPAK 50303, referred below as "foil"), Cryovac BYV200 or Cryovac P640B package. KAPAK 50303 is foil laminate container wherein the foil layer is aluminum foil. Cryovac BYV200 is a laminate containing a 0.0006 inch (or 0.015 millimeter) two-sided Saran-coated polyvinyl alcohol layer. The oxygen permeability of these two laminates is less than 0.02 cc per 100 square inch (or 0.02 cc per 645 square centimeters) per 24 hrs per atm per 72° F. (or 22° C.) and 0% humidity. Cryovac P640B is a laminate material comprising a 0.0006 in. (or 0.015 millimeter) Saran-coated, biaxially-oriented Nylon layer, an adhesive and a linear low density polyethylene sealant layer. The oxygen permeability of the material is about 8 to 15 cc per 100 square inches (or about 8 to 15 cc per 645 square centimeters) per 24 hours per atm at 72° F. (or 22° C.) and 0% humidity. The packaged blood substitutes were maintained at room temperature for about 418 days with periodic sampling of the concentration and/or levels of N-acetyl-L-cysteine (NAC), bis-N-acetyl-L-cysteine ($NAC_2$), total Hb (THb), oxygenated hemoglobin ($HbO_2$) and methemoglobin (metHb). The results are set forth in Table II.

TABLE II

Stability Data on Overwraps

| Day | Over-wrap | NAC (%) | $NAC_2$ (%) | THb (g/dl) | $HbO_2$ (%) | metHB (%) |
|---|---|---|---|---|---|---|
| 0 | Foil | 0.1515 | 0.008 | 10.7 | 4.1 | −0.2 |
| 0 | BYV200 | 0.1586 | 0.0139 | 10.7 | 8.8 | −0.3 |

TABLE II-continued

Stability Data on Overwraps

| Day | Over-wrap | NAC (%) | NAC$_2$ (%) | THb (g/dl) | HbO$_2$ (%) | metHB (%) |
|---|---|---|---|---|---|---|
| 0 | P640B | 0.1274 | 0.0829 | 11.7 | 5.7 | 1.1 |
| 43 | Foil | 0.1688 | 0.0155 | 11.3 | 3.3 | −0.3 |
| 43 | BYV200 | 0.1509 | 0.0365 | 11.1 | 2.7 | 0.3 |
| 43 | P640B | 0.0507 | 0.1927 | 11.2 | 5.6 | 6.2 |
| 117 | Foil | 0.1721 | 0.0136 | 11.7 | 2.6 | 0.0 |
| 117 | BYV200 | 0.1433 | 0.0238 | 11.9 | 3.0 | 0.1 |
| 117 | P640B | 0.0022 | 0.2355 | 12.5 | 12.7 | 30.7 |
| 180 | Foil | 0.1818 | 0.0108 | 12.1 | 2.9 | −0.1 |
| 180 | BYV200 | 0.1674 | 0.0327 | 12.5 | 2.5 | 0.2 |
| 180 | P640B | N.D. | 0.2259 | 12.8 | 18.2 | 49.6 |
| 418 | Foil | 0.15 | 0.05 | 11.6 | 4.5 | 1.2 |
| 418 | BYV200 | 0.17 | 0.04 | 11.8 | 3.7 | 0.5 |
| 418 | P640B | N.D. | 0.19 | 12.0 | −1.3 | 92.3 |

The above experiment was essentially repeated wherein a hemoglobin blood-substitute was overwrapped in a foil laminate package (KAPAK 50303). The packaged blood substitutes were maintained at room temperature for about 24 months with periodic sampling of the concentration and/or levels of N-acetyl-L-cysteine (NAC), bis-N-acetyl-L-cysteine (NAC$_2$), total Hb (THb), oxygenated hemoglobin (HbO$_2$) and methemoglobin (metHb). The results are set forth in Table III.

TABLE III

Stability Data on Foil Overwraps

| Month | NAC (%) | NAC$_2$ (%) | THb (g/dl) | HbO$_2$ (%) | metHB (%) |
|---|---|---|---|---|---|
| 0 | 0.16 | 0.04 | 13.1 | 4 | 3 |
| 3 | 0.13 | 0.04 | 13.4 | 3 | 2 |
| 6 | 0.14 | 0.03 | 13.3 | 3 | 2 |
| 9 | 0.15 | 0.03 | 13.2 | 4 | 2 |
| 12 | 0.13 | 0.06 | 13.3 | 5 | 2 |
| 18 | 0.14 | 0.05 | 13.2 | 3 | 2 |
| 24 | 0.14 | 0.02 | 13.3 | 3 | 2 |

EXAMPLE 3

Hemoglobin Blood-Substitute Storage: Primary Package

The hemoglobin blood-substitute, as prepared in Example 1 was packaged in an oxygen barrier primary package (E-13135 and E13242, American National Can). The construction of the primary package is discussed in detail above. The primary package is a laminate material comprising a medium density polyethylene layer, ethylene vinyl alcohol/nylon layer, and linear low density polyethylene sealant layer.

EXAMPLE 4

Hemoglobin Blood-Substitute Storage: Transparent Overwrap

The hemoglobin blood-substitute, as prepared in Example 1, packaged in a suitable primary package, was overwrapped in a transparent laminate package comprising a polypropylene layer, an ethylene vinyl alcohol layer and a polypropylene layer. An automated packaging machine (Tiromat) was used to generate the overwraps. The oxygen permeability of the material is about 0.00153 cc per 100 square inches (or 0.001153 cc per 645 square centimeters) per atm per day (at 25° C., and 100%/50% RH). The packaged blood substitute was maintained at 40° and 100%/60% RH for about 12 months and the concentration and/or levels of N-acetyl-L-cysteine (NAC), bis-N-acetyl-L-cysteine (NAC$_2$), total Hb (THb), oxygenated hemoglobin (HbO$_2$) and methemoglobin (met Hb) were measured. The results are set forth in Table IV. Maintenance of the samples at the elevated temperature of 40° C. for 12 months has the effect of storage for 24 months at 23° C.

TABLE IV

Accelerated Stability Data on Clear (EVOH) Overwrap

| Month | NAC (%) | NAC2 (%) | THb (%) | HbO$_2$ (%) | MetHB (%) |
|---|---|---|---|---|---|
| 0 | 0.15 | 0.02 | 13.4 | 2.4 | 0.8 |
| 3 | 0.12 | 0.06 | 13.3 | 2.5 | 2.0 |
| 6 | 0.06 | 0.13 | 13.5 | 2.3 | 3.9 |
| 9 | 0.06 | 0.19 | 13.7 | 3.0 | 5.6 |
| 12 | 0.02 | 0.20 | 13.9 | 3.7 | 7.9 |

EXAMPLE 5

Polymerized Hemoglobin Analysis

The endotoxin concentration in the hemoglobin product is determined by the method "Kinetic/Turbidimetric LAL 5000 Methodology" developed by Associates of Cape Cod, Woods Hole, Mass., J. Levin et al., *J. Lab. Clin. Med.,* 75:903–911 (1970). Various methods were used to test for any traces of stroma for example, a precipitation assay, immunoblotting, and enzyme-linked immunosorbent assay (ELISA) for a specific cell membrane protein or glycolipid known by those skilled in the art.

Particulate counting was determined by the method "Particulate Matter in Injections: Large Volume Injections for Single Dose Infusions", *U.S Pharmacopeia,* 22:1596, 1990.

To determine glutaraldehyde concentration, a 400 μl representative sample of the hemoglobin product was derivatized with dinitrophenylhydrazine and then a 100 μl aliquot of the derivative solution was injected onto a YMC AQ-303 ODS column at 27° C., at a rate of 1 ml/min., along with a gradient. The gradient consisted of two mobile phases, 0.1% trifluoroacetic acid (TFA) in water and 0.08% TFA in acetonitrile. The gradient flow consisted of a constant 60% 0.08% TFA in acetonitrile for 6.0 minutes, a linear gradient to 85% 0.08% TFA in acetonitrile over 12 minutes, a linear gradient to 100% 0.08% TFA in acetonitrile over 4 minutes hold at 100% 0.08% TFA in acetonitrile for 2 minutes and re-equilibrate at 45% of 0.1% TFA in water. Ultraviolet detection was measured at 360 nm.

To determine NAC concentration, an aliquot of hemoglobin product was diluted 1:1100 with degassed sodium phosphate in water and 50 μl was injected onto a YMC AQ-303 ODS column with a gradient. The gradient buffers consisted of a sodium phosphate in water solution and a mixture of 80% acetonitrile in water with 0.05% TFA. The gradient flow consisted of 100% sodium phosphate in water for 15 minutes, then a linear gradient to 100% mixture of 80% acetonitrile and 0.05% TFA over 5 minutes, with a hold for 5 minutes. The system was then re-equilibrated at 100% sodium phosphate for 20 minutes.

Phospholipid analysis was done by a method based on procedures contained in the following two papers: Kolarovic et al., "A Comparison of Extraction Methods for the Isolation of Phospholipids from Biological Sources", *Anal. Biochem.*, 156:244–250, 1986 and Duck-Chong, C. G., "A Rapid Sensitive Method for Determining Phospholipid Phosphorus Involving Digestion With Magnesium Nitrate", *Lipids*, 14:492–497, 1979.

Osmolarity was determined by analysis on an Advanced Cryomatic Osmometer, Model #3C2, Advanced Instruments, Inc., Needham, Mass.

Total hemoglobin, methemoglobin and oxyhemoglobin concentrations were determined on a Co-Oximeter Model #482, from Instrumentation Laboratory, Lexington, Mass.

$Na^+$, $K^+$, $Cl^-$, $Ca^{++}$, $pO_2$ concentrations were determined by a Novastat Profile 4, Nova Biomedical Corporation, Waltham, Mass.

Oxygen binding constant, $P_{50}$ was determined by a Hemox-Analyzer, TCS Corporation, Southhampton, Pa.

Temperature and pH were determined by standard methods known by those skilled in the art.

Molecular weight (M.W.) was determined by conducting gel permeation chromatography (GPC) on the hemoglobin products under dissociating conditions. A representative sample of the hemoglobin product was analyzed for molecular weight distribution. The hemoglobin product was diluted to 4 mg/ml within a mobile phase of 50 mM Bis-Tris (pH 6.5), 750 mM $MgCl_2$, and 0.1 mM EDTA. This buffer serves to dissociate Hb tetramer into dimers, that have not been cross-linked to other Hb dimers through intramolecular or intermolecular crosslinks, from the poly(Hb). The diluted sample was injected onto a TosoHaas G3000SW column. Flow rate was 0.5 ml/min. and ultraviolet detection was recorded at 280 nm.

The results of the above tests on veterinary (OXYGLOBIN™) and human Hb blood-substitutes, formed according to the method of invention, are summarized in Tables V and VI, respectively.

TABLE V

| PARAMETER | RESULTS |
|---|---|
| pH (18–22° C.) | physiologically acceptable pH |
| Endotoxin | <0.5 EU/ml |
| Sterility Test | Meets Test |
| Phospholipids[a] | <3.3 nm/ml |
| Total Hemoglobin | 12.0–14.0 g/dl |
| Methemoglobin | <15% |
| Oxyhemoglobin | <10% |
| Sodium, $Na^+$ | 145–160 mM |
| Potassium, $K^+$ | 3.5–5.5 mM |
| Chloride, $Cl^-$ | 105–120 mM |
| Calcium, $Ca^{++}$ | 0.5–1.5 mM |
| Boron | <10 ppm |
| Osmolality | 290–310 mOsm |
| Glutaraldehyde | <3.5 µg/ml |
| N-acetyl-L-cysteine | <0.2% |
| M.W. >500,000 | <15% |
| Unmodified Tetramer | <5% |
| Particulate Content >10µ | <12/ml |
| Particulate Content >25µ | <2/ml |

[a]measured in Hb before polymerization

TABLE VI

| PARAMETER | RESULTS |
|---|---|
| pH (18–22° C.) | Physiologically acceptable pH |
| Endotoxin | <0.5 EU/ml |
| Sterility Test | Meets Test |
| Phospholipids[a] | <3.3 nm/ml |
| Total Hemoglobin | 12.0–14.0 g/dl |
| Methemoglobin | <15% |
| Oxyhemoglobin | <10% |
| Sodium, $Na^+$ | 145–160 mM |
| Potassium, $K^+$ | 3.5–5.5 mM |
| Chloride, $Cl^-$ | 105–120 mM |
| Calcium, $Ca^{++}$ | 0.5–1.5 mM |
| Boron | <10 ppm |
| Osmolality | 290–310 mOsm |
| Glutaraldehyde | <3.5 µg/ml |
| N-acetyl-L-cysteine | ≦0.2% |
| M.W. >500,000 | ≦15% |
| M.W. ≦65,000 | <10% |
| M.W. <32,000 | <5% |
| Particulate Content >10µ | <12/ml |
| Particulate Content >25µ | <2/ml |

[a]measured in Hb before polymerization

Those skilled in the art will recognize, or be able to ascertain using no more than routine experimentation, many equivalents to the specific embodiments of the invention described herein. These and all other such equivalents are intended to be encompassed by the following claims.

The invention claimed is:

1. A method for preserving a packaged deoxygenated hemoglobin blood substitute comprising maintaining the packaged deoxygenated hemoglobin blood substitute in an oxygen barrier film overwrap package including a transparent laminate material, the transparent laminate material comprising a polyolefin layer and an oxygen barrier layer that includes ethylene vinyl alcohol, wherein the laminate has a thickness of between about 0.0254 and 0.254 millimeters, and an oxygen permeability of less than about 0.01 cubic centimeters per 645 square centimeters over 24 hours at one atmosphere and at about 23° C.

2. The method of claim 1, wherein the polyolefin layer and the oxygen barrier layer are co-extruded.

3. The method of claim 1, wherein the oxygen barrier film overwrap package comprises at least two sheets of laminate material, wherein at least one sheet of the overwrap package comprises said transparent laminate material and wherein at least one other sheet of the overwrap package comprises a foil laminate material.

4. The method of claim 3, wherein the overwrap package is produced by:
   a) forming said foil laminate to define at least one chamber;
   b) placing the packaged deoxygenated hemoglobin blood substitute into said chamber; and
   c) heat sealing the transparent laminate to the foil laminate, whereby said oxygen barrier film overwrap is formed, thereby containing the packaged deoxygenated hemoglobin blood substitute within the overwrap.

5. The method of claim 1, wherein the packaged deoxygenated hemoglobin blood substitute is maintained under a nitrogen, argon or helium atmosphere.

6. A preserved deoxygenated hemoglobin blood substitute, comprising:
   a) a packaged deoxygenated hemoglobin blood substitute; and
   b) an oxygen barrier film overwrap package comprising a transparent laminate material, the transparent laminate material comprising a polyolefin layer and an oxygen barrier layer that includes ethylene vinyl alcohol, wherein the laminate has an oxygen permeability of less than about 0.01 cubic centimeters per 645 square centimeters over 24 hours at one atmosphere and at about 23° C., wherein the packaged deoxygenated hemoglobin blood substitute is sealed within the overwrap package.

7. The preserved deoxygenated blood substitute of claim 6, wherein the polyolefin layer and the oxygen barrier layer are co-extruded.

8. The preserved deoxygenated blood substitute of claim 6, wherein the oxygen barrier film overwrap package comprises at least two sheets of laminate material, wherein at least one sheet of the overwrap package comprises said transparent laminate material and wherein at least one other sheet of the overwrap comprises a foil laminate material.

9. The preserved deoxygenated blood substitute of claim 8, wherein the overwrap package is produced by:
 a) forming said foil laminate to define at least one chamber;
 b) placing the packaged deoxygenated hemoglobin blood substitute into said chamber; and
 c) heat sealing the transparent laminate to the foil laminate, whereby said oxygen barrier film overwrap is formed, thereby containing the packaged hemoglobin blood substitute within the overwrap.

* * * * *